United States Patent [19]
Zdrojkowski et al.

[11] Patent Number: 5,685,296
[45] Date of Patent: Nov. 11, 1997

[54] FLOW REGULATING VALVE AND METHOD

[75] Inventors: Ronald J. Zdrojkowski, Pittsburgh; Frank V. Blazek, Monroeville; John Raymond Pujol, Pittsburgh, all of Pa.

[73] Assignee: Respironics Inc., Pittsburgh, Pa.

[21] Appl. No.: 426,644

[22] Filed: Apr. 21, 1995

Related U.S. Application Data

[63] Continuation of Ser. No. 99,703, Jul. 30, 1993, abandoned.
[51] Int. Cl.$^6$ .............. A62B 9/02; A62B 7/04; A61M 16/00; F16K 31/26
[52] U.S. Cl. .............. 128/205.24; 128/204.18; 128/204.23; 128/204.26
[58] Field of Search ........... 128/204.18, 204.21–204.23, 128/204.26, 205.24

[56] References Cited

U.S. PATENT DOCUMENTS

| | | | |
|---|---|---|---|
| 3,429,342 | 2/1969 | Garreti | 138/43 |
| 3,467,136 | 9/1969 | Masson | 137/489 |
| 3,473,571 | 10/1969 | Dugay | 137/625 |
| 3,474,831 | 10/1969 | Noakes | 138/43 |
| 3,592,237 | 7/1971 | Borschers | 138/43 |
| 3,948,289 | 4/1976 | Stephens | 138/37 |
| 3,951,379 | 4/1976 | Cornelius | 251/118 |
| 4,182,371 | 1/1980 | Moore | 137/624 |
| 4,234,013 | 11/1980 | Rikuta | 137/504 |
| 4,280,527 | 7/1981 | Pease | 137/343 |
| 4,351,510 | 9/1982 | Welker | 251/118 |
| 4,354,516 | 10/1982 | Newell | 137/98 |
| 5,148,802 | 9/1992 | Sanders et al. | 128/204.23 |
| 5,161,525 | 11/1992 | Kimm et al. | 128/204.23 |
| 5,239,995 | 8/1993 | Estes et al. | 128/204.23 |

OTHER PUBLICATIONS

7200 Series, Catalog A–0AA493–02 (Jul. 1988), Bennett Group, 2310 Camino Vida Roble, Carlsbad, CA 92009.

7200a, "Option #50 Flow–by", Form #AA–1144 (Jan. 1987), Bennett Group, 2310 Camino Vida Roble, Carlsbad, CA 92009.

"Effect on the Work of Breathing . . . ", Form AA–1495 (Nov. 1989), Bennett Group, 2310 Camino Vida Roble, Carlsbad, CA 92009.

*Primary Examiner*—Kimberly L. Asher
*Attorney, Agent, or Firm*—J. Stewart Brams

[57] ABSTRACT

A flow regulating system including a valve and a method for maintaining a constant gas flow rate through a patient circuit to ambient exhaust at varying gas pressure by means of differential gas pressure applied to opposed sides of a valve diaphragm.

3 Claims, 2 Drawing Sheets

FLOW REGULATING VALVE AND METHOD

This is a continuation of application Ser. No. 08/099,703 filed on Jul. 30, 1993, now abandoned.

BACKGROUND OF THE INVENTION

In the valve arts a variety of valves are known which are intended to provide fluid flow at varying fluid pressures. The naturally occurring relationship of fluid flow to pressure (flow is proportional to the square root of pressure) can be regarded as unacceptable in a variety of technical contexts. For example, in medical ventilators used to assist patient breathing, and in similar devices used to supply breathing gas to a person for other reasons, it has been common practice to incorporate a fixed leak (i.e. a leak path of fixed cross-sectional area), especially in single tube circuits, to flush away the gas exhaled by the patient into the gas supply stream before the next patient inhalation begins. It is also known to utilize some such systems with an exhalation pressure lower than the inhalation pressure. In this case, the size of the fixed leak needed to flush exhaled gas from the supply tube under the low pressure conditions of exhalation may be so large that the flow rate through the fixed leak at higher pressure, as during inhalation, would result in enormous waste of supply gas during inhalation. For example, in one known gas supply system, a leak flow rate of about 20 liters per minute (L/min.) may be sufficient to flush exhalation gas from the supply conduit prior to the subsequent patient inhalation. A fixed orifice which will support a 20 L/min. leak at the system exhalation pressure of 2 cm $H_2O$ will pass approximately 77.5 L/min. at 30 cm $H_2O$. Such a high leak rate during inhalation is not only wasteful of medical resources, but is also not required for any therapeutic reason.

It would be preferable that the leak which is provided to flush exhaled gas from such a system not increase appreciably with increases in pressure. Indeed, it might well be preferable that the leak flow rate during inhalation, if that is the higher pressure part of the system operating cycle, should be less than the leak flow rate during exhalation since there is no need to flush exhaled gas during inhalation. A varying system leak flow rate can also complicate operation of such known respiratory gas supply systems as those which are controlled in part by monitoring of the average system leak.

Among the prior art of valves purporting to regulate flow by means of pressure actuated regulators are those disclosed in U.S. Pat. Nos. 3,467,136, 3,474,831, 3,592,237, 3,948,289 and 3,951,379. Other flow regulating valves are disclosed in U.S. Pat. Nos. 3,429,342, 3,473,571, 3,770,104, 4,182,371, 4,234,013, 4,280,527, 4,351,510 and 4,354,516.

SUMMARY OF THE INVENTION

The present invention contemplates a novel and improved constant flow valve for use in regulating gas flow rates in a breathing gas supply apparatus to thereby maintain a constant gas flow rate through the valve under varying pressure conditions. The valve is adapted to operate reliably under the pressure and flow conditions encountered in such systems. For example, one embodiment of the novel valve is for use as a patient-end exhaust valve to provide a continuous, controlled leak for flushing exhaled gas from the system supply conduit. This valve is operable to provide a regulated, essentially constant volumetric flow rate of, for example, approximately 25 L/min. over a low pressure range up to 50 cm $H_2O$ pressure (that is, a pressure range of approximately 1 to 50 cm $H_2O$ gas pressure).

Another embodiment of the novel valve is well adapted for use at the inlet of a blower which provides a supply of breathing gas such as ambient air within a specified range of positive pressures above ambient atmospheric pressure for breathing by a user. This valve is operable in a similar range of pressures but preferably at higher flow rates to maintain an essentially constant system flow rate over a range of operating pressures. The blower inlet valve according to this invention is useful for the same reasons as set forth above for the exhaust or exhalation valve. That is, the system typically must operate within a range of pressures in which a constant flow rate could be difficult to achieve without the use of such a control valve. For the blower inlet valve specifically, the required system pressure would call for a fairly large blower to generate the needed pressure without undue mechanical wear; however, a large blower would also tend to generate excessive flow rates. In order to avoid having to employ a smaller blower which could be both noisier and less reliable, the blower inlet valve of this invention restricts a blower inlet flow so that a desired system flow rate and operating pressure range may be achieved with a larger blower.

In all embodiments of the valve disclosed herein a free floating, resilient, flexible diaphragm is movable with respect to a regulating element in a valve casing or housing to control the gas flow rate through the valve.

Accordingly, it is one object of the invention to provide a novel and improved flow regulating valve.

Another object of the invention is to provide a novel and improved breathing gas flow supply apparatus.

A further object of the invention is to provide a novel and improved method of administering breathing gas for breathing by a person.

A more specific object of the invention is to provide a novel flow regulating valve having as a regulating member a thin membranous diaphragm which is flexible for movement with respect to a gas flow regulating element in response to differential pressures applied to opposed sides of the membrane.

BRIEF DESCRIPTION OF THE DRAWINGS

These and other objects and further advantages of the invention will be more readily understood upon consideration of the following detailed description and the accompanying drawings, in which.

DESCRIPTION OF THE PREFERRED EMBODIMENTS

Figure 1:
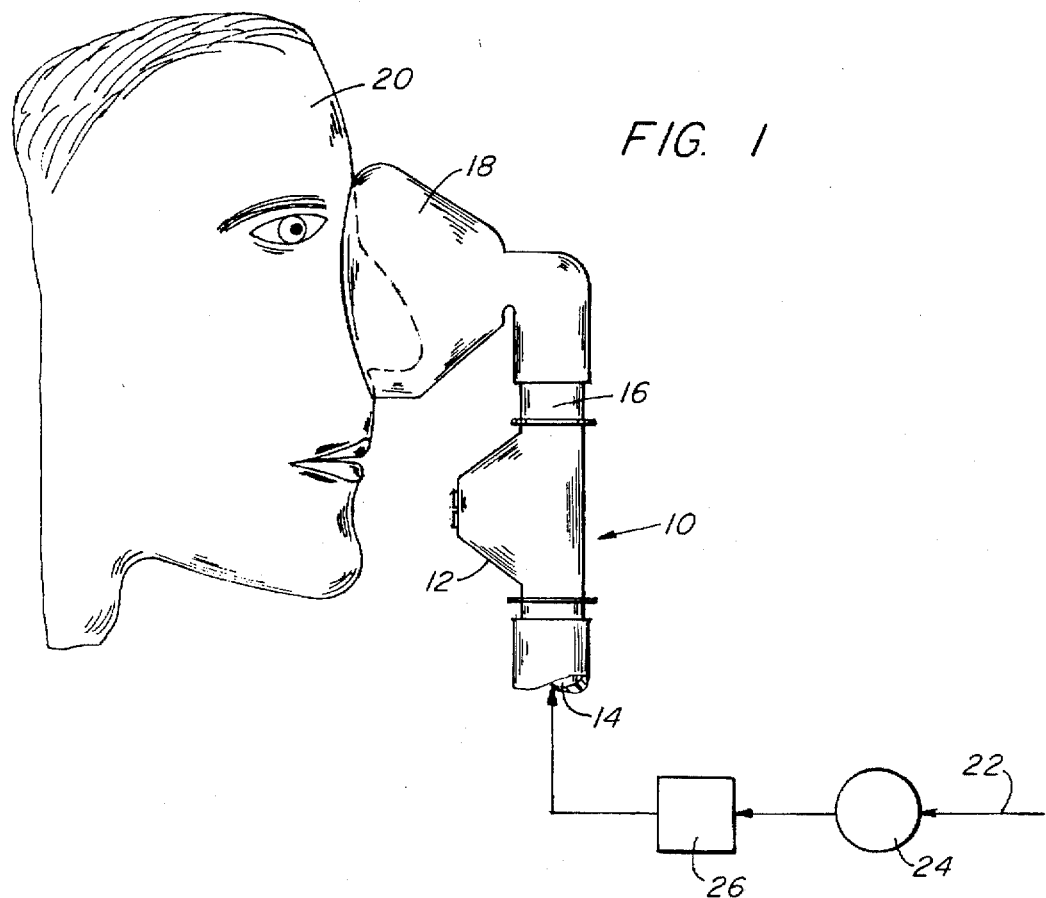
FIG. 1 is a partially schematic illustration of a breathing gas delivery system including a valve according to the present invention.

Referring to FIG. 1, there is generally indicated at 10 a breathing gas delivery system which is operable according to the method of the present invention. Operation of system 10 is facilitated by inclusion therein of a valve 12 mounted for communication with the flow passage 14 of a user gas supply conduit assembly 16 which includes a mask 18 that is adapted to confront a portion of the user's face, for example the nose area, of user 20. Of course, mask 18 may alternatively be a full face mask enclosing both the nose and mouth areas, or any of a variety of other suitable user interfaces.

System 10 further includes a breathing gas flow source 22, for example the ambient atmosphere, which delivers gas to a pressure and flow generating apparatus 24, a blower for example. System 10 also includes pressure controlling apparatus 26 which preferably is operable to vary and control the pressure of breathing gas flow which passes to user 20 via supply conduit 16.

In one presently preferred embodiment of the invention, apparatus 24 and 26 may suitably be entirely similar to the gas flow supply and pressure control apparatus disclosed in U.S. Pat. No. 5,148,802, the entire disclosure of which is now incorporated herein and made a part hereof by reference.

A system 10 which is operable according to the description of the hereinabove referenced U.S. Pat. No. 5,148,802 delivers a flow of breathing gas to user 20 at alternately higher and lower pressures, both at least equal to ambient atmospheric pressure, the higher pressure being supplied during inhalation and the lower pressure being supplied during exhalation.

In such a system 10, valve 12 is operable to provide gas exhaust or purge flow from conduit 16 to a suitable disposal facility, for example the ambient atmosphere, at an essentially fixed flow rate irrespective of the supply pressure within conduit 16. In this regard, it is noted that the supply pressure preferably is to be as low as possible, for example in the range of 1 to 50 cm $H_2O$. Higher pressure breathing gas is used in medical treatment, but administration of such higher pressures generally is not compatible with a mask interface such as mask 18. In addition, higher pressure delivery could increase system wear and energy costs, and could contribute to user discomfort thus reducing user compliance. The specified pressure operating range of 1 to 50 cm $H_2O$ is applied with a preferred exhaust gas average volumetric flow rate of approximately 25 L/min. over the specified pressure range. An average volumetric flow rate in the range of approximately 17 L/min. to approximately 40 L/min. is consistent with expected uses of the valve 12 as an exhaust regulator. When the alternative valve embodiment is used as an inlet flow regulator as described hereinbelow, average volumetric flow rate in the range of approximately 5 L/min. to approximately 300 L/min. would be consistent with the anticipated use of the valve.

Figure 2:
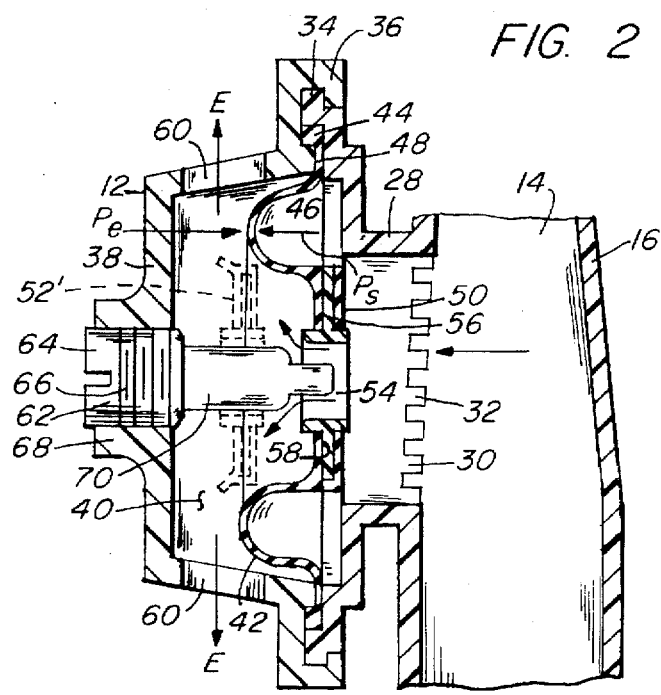
FIG. 2 is a sectioned side elevation of a valve substantially similar to the valve shown in the system of FIG. 1.

For the system shown in FIGS. 1 and 2, valve 12 is employed as an exhalation valve to reduce concentrations of $CO_2$ in supply conduit 16. That is, as user 20 exhales into mask 18 the gas supply within conduit 16 is enriched with $CO_2$ from the user's exhaled breath. In order to ensure the user does not re-breath $CO_2$-rich supply air with the next inhalation, valve 12 provides for continuous exhaust of supply gas, including $CO_2$ enriched gas which occurs on user exhalation.

Valve 12 includes a base portion 28 which communicates with passageway 14 through an interface 30 which may include a suitable screen 32 or similar means to capture fluids that may be entrained in the gas in passage 14.

Base 28 as shown is of a generally stepped annular configuration and may be formed, for example, of molded plastic. Alternatively, the base 28 may take the form of a contoured cone. For the embodiment shown an outer, generally annular engagement portion 34 of base 28 is suitably formed for interlocking cooperation with a corresponding engagement portion 36 of a valve body member 38, also of a generally stepped annular form and also preferably fabricated as a molded plastic structure. For example, engagement portions 34 and 36 may be mutually cooperable to provide a bayonet lock type interlocking engagement or a snap-fit interlock.

The valve portions 28 and 38, as shown, extend in axially opposed directions from the mutually engaged portions 34 and 36 to define within the bounds of portions 28 and 38 a space 40 which confines therein an assembly of flow regulating elements.

More specifically, a resilient diaphragm 42, which may conveniently be of a generally annular form, for example, resides within space 40 intermediate valve portions 28 and 38, and includes a radially outer peripheral bead portion 44 which is captured adjacent the interlocking portions 34 and 36 intermediate base 28 and housing 38 to fixedly and sealingly clamp the radially outer perimeter of diaphragm 42.

Moving radially inward from bead portion 44, diaphragm 42 further includes a generally annular formed bellows portion 46, a radially extending connecting portion 48 which extends intermediate bead portion 44 and bellows portion 46, and a central insert receiving portion 50 which projects radially inwardly of bellows portion 46. A relatively rigid central insert 52 of molded plastic, for example, includes a central axial opening 54 located preferably in coaxial relationship with respect to diaphragm 42, and a radially outwardly extending flange portion 56 which is sealingly engaged within a corresponding annular groove 58 formed in the insert receiving portion 50 of diaphragm 42. Flange 56 may be glued or physically interlocked, as deemed suitable, within groove 58 for retention of insert 52 with respect to diaphragm 42.

As noted, diaphragm 42 is a resilient member preferably of rubber-like material such as silicone rubber, for example. As such, when deformed the material of diaphragm 42 has an inherent tendency to spring or resile to an undeformed state, for example as shown in FIG. 2. The deformation of diaphragm 42 which will occur in operation is occasioned by a pressure differential imposed on opposite sides of the diaphragm, the supply pressure being applied to the supply conduit side of the diaphragm as indicated by arrow $P_s$, and atmospheric pressure being applied to the opposed or exhaust side thereof as indicated by arrow $P_e$.

To accommodate such pressure application, housing 12 includes one or more open exhaust ports 60 through which exhaust gas flows, as indicated by arrows E, from space 40. Exhaust ports 60 are sized to be large enough that in operation the flow through the exhaust ports 60 does not impose any pressure $P_e$ significantly above ambient atmospheric pressure on the exhaust side of diaphragm 42.

With the pressure differential between atmospheric and supply pressure acting on opposed sides of diaphragm 42 as described, the diaphragm 42 tends to deform by axial movement to the left as viewed in FIG. 2. This motion tends to deform bellows portion 46, which deformation results in an internal restoring or resiling force within diaphragm 42 tending to oppose the deformational movement. Thus, for a given pressure differential, insert 52 will assume a predeterminable position displaced to the left of the neutral position, for example as shown in FIG. 2 at 52'. The position 52' will be determined by the point of balance between the force of the net pressure differential applied to the diaphragm 42, and the restoring or resiling force evolved by deformation of the diaphragm 42.

For a greater pressure differential, the diaphragm 42 will deform still further as insert 52 moves further to the left of position 52' until reaching a point where the greater pressure differential is balanced by a correspondingly greater resiling or restoring force. Similarly, for a lesser pressure differential, insert 52 will move to the right of position 52' to the point of balance where the lesser pressure differential is just great enough to overcome the inherent resiling or restoring force of the diaphragm 42.

In order to utilize the above-described structure to achieve a constant exhaust flow rate E over the full range of supply pressures, valve 12 is further provided with a tapered regulating pin 62 having a head portion 64 with formed threads 66 which are threadedly engaged within a cooperating, internally threaded portion 68 of housing 38. With pin 62 thus retained with respect to housing 38, a body portion 70 of pin 62 projects coaxially toward insert 52 and through opening 54 for cooperation therewith to regulate exhaust flow through the valve 12. The insert 52 and pin 62 are dimensioned to provide a clearance between them for any relative position, such as position 52', that gas flow through the clearance between pin 62 and insert 52 is maintained essentially at the regulator flow rate for any pressure differential occurring within the specified range of operating pressures.

Pin body portion 70 may be an elongated, generally cylindrical and slightly tapered member about which the insert 52 is coaxially received with opening 54 having a continuous radial clearance from the pin body portion 70. However, as the body portion 70 tapers in the axial direction toward insert 52 from a larger to a smaller diameter, each different axial position of insert 52 encompassing pin body portion 70 provides an exhaust valve port of different cross sectional area. More specifically, for positions of insert 52 successively further to the left with respect to pin body portion 70, the cross sectional area of the exhaust port formed radially between opening 54 and pin body portion 70 is successively smaller.

Accordingly, larger supply side pressure tending to impose greater rates of exhaust gas flow through passage 54 are countered by corresponding reductions in the effective cross sectional area of passage 54 as insert 50 is moved to the left by the higher pressure, whereby a balance may be obtained such that the net exhaust gas flow rate E remains essentially constant over the full range of system operating pressures. That is, for any given system operating pressure, the resulting pressure differential between the opposed sides of diaphragm 42 moves the diaphragm 42 to a predeterminable position with respect to pin body 70. Insert 52 cooperates with the pin body portion 70 at each attainable position to limit exhaust flow through the passage 54 in a manner that the available supply pressure, acting through the available passage 54 cross sectional area, always results in an essentially fixed, predetermined exhaust flow rate.

In order to adjust exhaust flow to a flow rate deemed suitable, pin 62 may be adjusted axially with respect to insert 52 by rotation thereof in either the clockwise or counter-clockwise direction whereby the threaded engagement of threads 66 in housing portion 68 will move pin body portion 70 axially toward or away from insert 52 to thereby decrease or increase the exhaust flow rate for any given supply pressure value. Adjustment of pin 62 thus permits the selection of a valve flow rate which will be effective over the working pressure range, for example the specified 1 to 50 cm $H_2O$ range.

Of course, all necessary design expedients are to be observed in the construction of valve 12. For example, in no case should the elastic deformation of bellows portion 46 ever obstruct exhaust ports 60, nor should the geometry or structure of valve 12 in any other way permit a pressure in any significant amount greater than ambient atmospheric pressure to be applied to the exhaust side of diaphragm 42.

It is noted that valve 12 as described above is a contactless valve in which the movable insert 52, never contacts the cooperating regulating element, pin 62, in normal operation. Rather, insert 52 is movable axially with respect to pin body portion 70 but always in radially spaced relation to it. Accordingly, diaphragm 42 is free to float under its inherent springing or resiling force. Its interaction with insert 52 and pin 62 in regulating exhaust flow through the valve does not result in any frictional forces or other resistance or restraint, for example sticking between relatively movable parts caused by deposit of body fluids on regulating element surfaces.

The only forces tending to move or adjust the position of insert 52 with respect to pin 62 are the differential pressures $P_s$ and $P_e$ applied to opposed sides of diaphragm 42, and the internal restoring or resiling force of the diaphragm.

Figure 3:
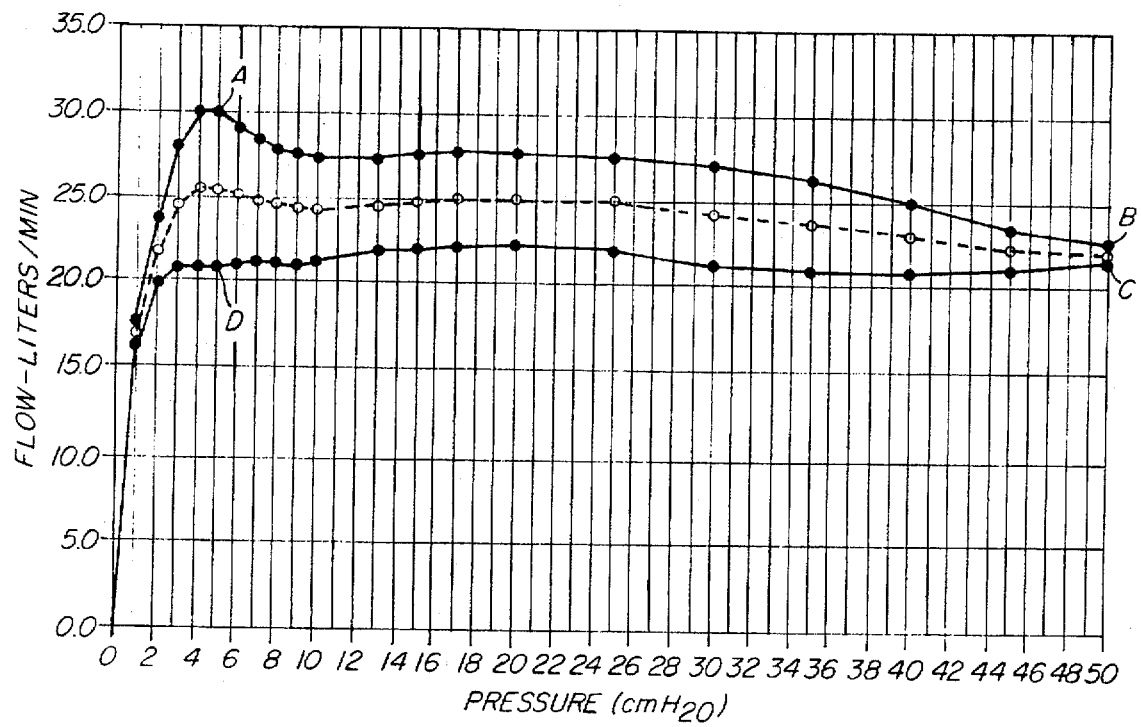
FIG. 3 is a plot of pressure versus flow rate for a valve of the present invention.

FIG. 3 illustrates a plot of exhaust flow as a function of system supply pressure for the valve and system of FIGS. 1 and 2, from which it may be seen that for nearly the entire range of operating pressures from 1 to 50 cm $H_2O$, the exhaust flow rate remains essentially constant, or varies only within a very narrow range of values. More specifically, FIG. 3 illustrates the hysteresis effect exhibited by the movable diaphragm of the above-described valve. The hysteresis effect, which reflects energy dissipated in moving or deforming the diaphragm material, tends to oppose the motion of the diaphragm as it moves in response to a changing pressure differential applied thereto. Thus, when pressure $P_s$ increases to a given level, the final position of the diaphragm will be slightly different than when the pressure $P_s$ decreases to the same given level. Accordingly, the regulated flow through the valve for such a given pressure level may be slightly higher or slightly lower than the desired average flow, depending upon the pattern of pressure changes preceding establishment of the given pressure level. Nevertheless, as FIG. 3 clearly illustrates, the flow through the disclosed valve remains essentially constant, within specified limits, over substantially the entire range of operating pressures for the valve. For example, with pressure increasing from approximately 5 cm $H_2O$ (point A, FIG. 3) to approximately 50 cm $H_2O$ at point B the gas flow rate through the valve remains in a fairly narrow range of values between approximately 30 L/min. and 22 L/min. Similarly, as pressure decreases from 50 cm $H_2O$ at point C to 5 cm $H_2O$ at point D, the gas flow rate through the valve remains in a very narrow range of values between approximately 21 L/min. and 22 L/min.

It will be appreciated that the relationship of gas pressure to flow rate illustrated by FIG. 3 is merely exemplary. Other ranges of flow rate variation within the specified pressure range would be equally suitable for purposes of the present invention. Further, even though the flow rate of gas through the valve does vary with changes in pressure as shown in FIG. 3, as noted above the flow rate variation occurs within a relatively narrow range of values and is wholly unlike the normally expected relationship of pressure to flow rate as set forth hereinabove. Accordingly, for emphasis it is repeated that the flow rates exhibited in FIG. 3, and comparable alternative patterns of flow rate variation with pressure change, are regarded in the context of this invention as being essentially constant flow rates throughout the illustrated range of pressure values.

The hysteresis effect illustrated by FIG. 3 is generally more prevalent in the above-described valve than in the alternative valve embodiment disclosed hereinbelow with reference to FIGS. 4 and 5. Thus, for the FIGS. 4 and 5 embodiment, in general a smaller difference between upper and lower flow limits would be expected at any given operating pressure.

Figure 4:
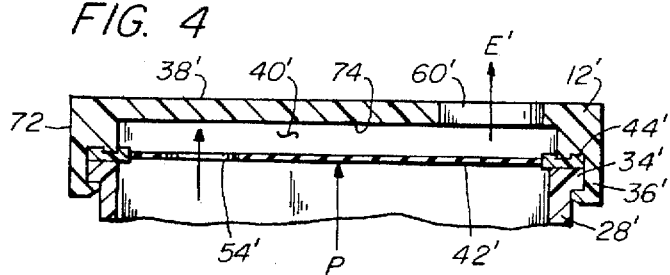
FIG. 4 is a sectioned side elevation of one alternative embodiment of a valve according to the present invention.

In FIG. 4 there is shown in generally schematic form an alternative embodiment of an exhaust valve for the system of FIG. 1. In FIG. 4, valve 72 includes a base portion 28' which has a generally annular engagement portion 34' for cooperable engagement with a corresponding engagement portion 36' of a valve housing 12', for example a bayonet engagement or a snap-fit. The base 28' and housing 12' captively retain a radially outer bead portion 44' of a diaphragm 42'. A space 40' is defined within the confines of base 28' and housing 12', on the exhaust side of diaphragm 42'. An exhaust port 60' is formed in housing 12' for communication between space 40' and the ambient atmosphere to thereby accommodate exhaust flow E'. Supply pressure P is applied to the side of diaphragm 42' which is open to supply flow to thereby drive exhaust flow through an opening 54' formed in diaphragm 42'. The flow control characteristic of the valve shown in FIG. 4 does not require gas flow to pass through an opening in the flexible diaphragm itself. Any suitable bypass flow passage around diaphragm 42' may be provided, so long as the pressure differential actuation of diaphragm 42' is maintained and the resultant flow control scheme effected so that flow through the valve remains essentially constant over a desired range of valve operating pressures.

Diaphragm 42' is formed of a flexible material having a quality or character of resilience similar in all salient respect to that of diaphragm 42 as above described. When supply pressure P is applied to the supply side of diaphragm 42' a pressure gradient is applied in chamber 40' which varies essentially from pressure P at opening 54' to ambient pressure at exhaust port 60'. This pressure gradient imposes a net force on the side of diaphragm 42' facing chamber 40' that is less than the force of pressure P acting on the opposed side of diaphragm 42'. In response, diaphragm 42' deforms toward the lower pressure side thus restricting exhaust flow E' by limiting the cross sectional area available for exhaust flow between diaphragm 42' and a confronting inner transverse wall surface portion 74 of valve housing 38'. This limitation of the exhaust valve flow area operates to maintain a constant exhaust flow rate E' over a wide range of operating pressures P as above described with reference to FIG. 2. That is, pressure P and the opposed pressure gradient in chamber 40' result in a force differential tending to deform diaphragm 42' outward toward wall 74 to a position of balance where the net differential pressure force is balanced by the internal restoring or resiling force of diaphragm 42'. Thus, for any pressure force P within the range of operating pressures, a resulting exhaust valve cross sectional flow area is established. Increases in pressure P deform diaphragm 42' further outward toward wall 74 thus further decreasing the cross sectional area available for exhaust flow, and thereby maintaining a constant exhaust flow rate over a wide range of operating pressures.

A further embodiment of the invention is disclosed in FIG. 5 as an inlet valve for blower 24 of FIG. 1, although the valve can also be used as an exhaust valve in the manner described hereinabove with reference to FIGS. 1-4. In FIG. 5, a valve 12" includes a base portion 28" which is engagable with a housing 38" such as above described with reference to FIG. 4 to captively retain a radially outer bead portion 44" of an imperforate diaphragm 42". Diaphragm 42" is of flexible and resilient material essentially as above described with reference to FIGS. 4 and 2.

An opening 76 communicates between the ambient atmosphere and a space 40" within the confines of base 28" and housing 38" on the atmospheric or low pressure side of diaphragm 42". The portion of space 40" on the opposed side of diaphragm 42" forms a flow channel 78 for inlet gas flow I from a source, for example the ambient atmosphere, through an opening 80 formed in valve base portion 28". A second flow port or opening 82 communicates between channel 78 and blower 24, and is thus indicated as the gas flow source 22 referred to in FIG. 1.

Figure 5:
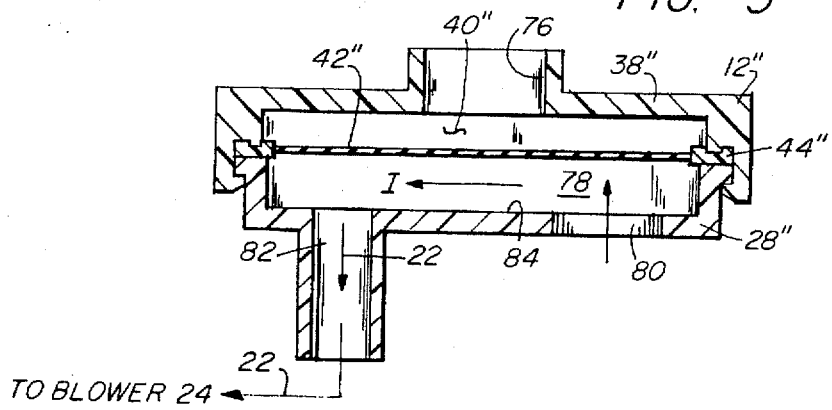
FIG. 5 is a sectioned side elevation of another alternative embodiment of a valve according to the present invention.

In the FIG. 5 embodiment, diaphragm 42" is deformable under a pressure differential applied to opposed sides thereof just as in the other described embodiments; however, in this case ambient atmospheric pressure is applied to one side of diaphragm 42" via port 76 and a reduced pressure, less than ambient atmospheric pressure, is applied within channel 78 by virtue of the inlet of blower 24 being connected to port 82. The cross sectional area of port 80 is suitably sized with respect to the demand flow rate of blower 24 to impose a relatively reduced pressure below ambient atmospheric pressure within space 78. The resulting pressure differential applied to diaphragm 42" tends to deform the diaphragm toward an inner transverse wall 84 of valve base portion 28".

The valve of FIG. 5 may perform a different function from the other valve embodiments described hereinabove. It can permit the use of a large, slow speed blower for the blower 24. This is preferred because a comparatively large blower generally is required to generate adequate supply pressure for system operation with minimal mechanical wear. Although a smaller blower can generate the required pressure, the wear rates are greater, the blower mechanisms tend to be noisier, and the system thus would be subject to lower levels of user acceptance and shorter service life. One example of a system in which long term reliability and quiet operation both may be important factors is an apparatus for treating obstructive sleep apnea by providing the patient a continuous supply of breathing gas under elevated pressure. As sleep apnea is generally regarded not as a disease process but as a structural anomaly of a person's airway, it may well require use of such an apparatus on a long term basis during one's sleeping hours. A system powered by a small, noisy blower could be as much a disturbance to the patient's sleep as the sleep apnea condition itself. Further, as the blower may well be one of the costlier system components, a relatively shorter service life could be uneconomical because, as noted a patient may well have to rely on use of the apparatus for a term of very long duration.

Accordingly, to generate the pressures required a larger, slower operating blower would in general be preferable to a smaller, higher speed blower; however, since a larger blower will tend to generate larger flows at the required supply pressure, a supply flow restrictor such as the valve of FIG. 5 is desirable to permit the use of a larger size, slower operating blower.

The valve of FIG. 5 can accommodate flow rates up to, for example, 300 L/min., although much lower flow rates may commonly be called for by the specific gas supply therapy being undertaken.

According to the method of the present invention, a supply of breathing gas is provided to a user 20 (FIG. 1) by the described system at varying pressures whose magnitude may be governed in specified ways with respect to the user's successive inhalation and exhalation breathing cycles. In conjunction with the varying supply pressure, a constant exhaust flow is provided to expel gas from the supply stream at an essentially constant flow rate irrespective of the operating pressure within the supply stream. The supply stream pressure may vary not only in response to pressure control imposed by pressure controller 26, but in addition in response to the user's breathing as the breathing cycle proceeds successively from inhalation to exhalation to inhalation. The supply stream pressure tends to vary in response to user breathing most particularly near the mask 18 because the continuing variation in user effort on both inhalation and exhalation, and the resulting continuous variation in gas flow rate and direction, create waves of pressure and flow rate fluctuation which are carried from the user through supply conduit 16 to pressure regulator 26. These waves of pressure and flow variation always reach valve 12 before they reach pressure regulator 26, and thus valve 12 reacts before regulator 26 can respond in regulating the pressure within supply conduit 16.

With these pressure and flow variations superimposed upon the pressure supplied via conduit 16 from pressure regulator 26, the maintenance of a continuous, constant exhaust flow rate is a novel methodology utilized in conjunction with varying supply and/or user airway pressure.

The method of the invention therefore may be broadly characterized as: providing a supply of breathing gas under pressure for breathing by a user by providing a flow of breathing gas through a supply path to the airway of the user while maintaining the pressure of the breathing gas flow within the supply path at selected elevated pressures which vary in magnitude over a given time interval, and simultaneously passing an essentially continuous exhaust flow of gas from the supply path at an essentially constant flow rate throughout the same time interval.

According to the above description, we have invented a novel and improved valve, gas supply apparatus and method for use in the supplying of breathing gas to a user. Notwithstanding the description hereinabove of certain presently preferred embodiments of the invention, we have contemplated various alternative and modified embodiments thereof. Such modifications would also occur to others versed in the art, once they were apprised of our invention.

Accordingly, we intend that the invention should be construed broadly and limited only by the scope of the claims appended hereto.

We claim:

1. In a method of providing a supply of breathing gas under pressure for breathing by a user, the steps comprising:

providing a flow of such breathing gas through a supply path which extends from a breathing gas source to the airway of the user;

maintaining a varying pressure of said breathing gas flow within said supply path at selected elevated pressures which vary in magnitude over a given time interval; and passing an essentially continuous exhaust flow of said varying pressure breathing gas from said supply path to ambient pressure at an essentially constant flow rate throughout said given time interval.

2. The method as set forth in claim 1 wherein said essentially continuous exhaust flow of gas is maintained at a flow rate essentially equal to the average flow rate of said supply flow of breathing gas within said supply path.

3. In a method of continuously supplying breathing gas at elevated pressure from a breathing gas source for breathing by a user, the steps comprising:

providing a continuous flow of such breathing gas through a supply path which extends from the breathing gas source to the airway of the user;

maintaining the pressure of said breathing gas flow at selected elevated pressures which vary in magnitude during a given time interval to provide a continuous flow of varying pressure breathing gas within said supply path for breathing by the user; and continuously passing a portion of said varying pressure breathing gas by way of a valve means from said supply path to an ambient pressure environment at an essentially constant flow rate throughout said given time interval;

whereby said continuous supplying of breathing gas exhibits the characteristics of varying pressure of said breathing gas flow and simultaneously an essentially constant rate of flow of said breathing gas from said supply path to said ambient pressure environment.

* * * * *